(12) United States Patent
Lavender et al.

(10) Patent No.: US 11,673,158 B1
(45) Date of Patent: Jun. 13, 2023

(54) METHOD AND APPARATUS FOR COATING A DRINKING STRAW

(71) Applicants: Jon Kyle Lavender, Fort Myers, FL (US); Alex Jon Lavender, Fort Myers, FL (US)

(72) Inventors: Jon Kyle Lavender, Fort Myers, FL (US); Alex Jon Lavender, Fort Myers, FL (US)

( * ) Notice: Subject to any disclaimer, the term of this patent is extended or adjusted under 35 U.S.C. 154(b) by 0 days.

(21) Appl. No.: 17/673,452

(22) Filed: Feb. 16, 2022

(51) Int. Cl.
| | |
|---|---|
| *B05C 11/10* | (2006.01) |
| *B05C 3/09* | (2006.01) |
| *B05C 11/11* | (2006.01) |
| *A47G 21/18* | (2006.01) |
| *A61K 45/06* | (2006.01) |
| *D21H 19/82* | (2006.01) |
| *D21H 19/38* | (2006.01) |
| *A61K 31/05* | (2006.01) |
| *A61K 31/352* | (2006.01) |
| *D21H 23/66* | (2006.01) |

(52) U.S. Cl.
CPC .......... *B05C 11/1039* (2013.01); *A47G 21/18* (2013.01); *A61K 31/05* (2013.01); *A61K 31/352* (2013.01); *A61K 45/06* (2013.01); *B05C 3/09* (2013.01); *B05C 11/11* (2013.01); *D21H 19/38* (2013.01); *D21H 19/822* (2013.01); *D21H 23/66* (2013.01)

(58) Field of Classification Search
None
See application file for complete search history.

(56) References Cited

U.S. PATENT DOCUMENTS

| | | | | |
|---|---|---|---|---|
| 523,099 | A * | 7/1894 | Barber | C25D 17/28 118/423 |
| 536,402 | A * | 3/1895 | Spaulding | C06F 1/26 118/423 |
| 864,092 | A * | 8/1907 | Burns | B05C 3/10 118/423 |
| 1,210,442 | A * | 1/1917 | Elliott | B05C 1/02 118/423 |
| 1,274,830 | A * | 8/1918 | Wood | B05C 11/06 118/425 |
| 1,759,502 | A * | 5/1930 | Sperry | B05C 3/10 425/269 |
| 1,794,751 | A * | 3/1931 | Beadle | A23B 5/06 118/63 |

(Continued)

FOREIGN PATENT DOCUMENTS

WO 9909871 A 3/1999

*Primary Examiner* — Jethro M. Pence
(74) *Attorney, Agent, or Firm* — NK Patent Law

(57) ABSTRACT

A method for coating a paper drinking straw, an apparatus for coating a paper drinking straw, and a coated drinking straw assembly are disclosed. The apparatus includes a dipping tank containing a liquid bath for coating a straw when submerged in the liquid and a straw engagement means for submerging the straw in the bath. The method includes receiving an uncoated paper drinking straw and submerging the straw in a bath containing a water-resistant and/or a water-soluble coating. The drinking straw assembly includes an elongate tubular body and a coating that has been applied to all surfaces of the straw by submerging the body in a bath containing the coating.

26 Claims, 7 Drawing Sheets

(56) References Cited

U.S. PATENT DOCUMENTS

| | | | | |
|---|---|---|---|---|
| 2,153,561 A * | 4/1939 | Hothersall | | B05C 3/10 |
| | | | | 118/63 |
| 2,182,364 A * | 12/1939 | Smith | | C21D 1/44 |
| | | | | 118/406 |
| 2,316,972 A * | 4/1943 | Pond | | C23C 18/1632 |
| | | | | 427/232 |
| 2,321,397 A * | 6/1943 | Koch | | D21H 23/32 |
| | | | | 118/423 |
| 2,640,584 A * | 6/1953 | Robb | | B05C 3/10 |
| | | | | 118/57 |
| 2,755,205 A * | 7/1956 | Zimmerman | | B28B 11/045 |
| | | | | 427/232 |
| 2,755,507 A * | 7/1956 | Heller | | B05C 9/14 |
| | | | | 425/269 |
| 3,109,751 A * | 11/1963 | Kingston | | B05C 3/02 |
| | | | | 118/425 |
| 5,895,529 A * | 4/1999 | Foley | | B05C 13/02 |
| | | | | 427/430.1 |
| 6,514,340 B1 * | 2/2003 | Momose | | F26B 21/10 |
| | | | | 118/69 |
| 7,381,273 B2 * | 6/2008 | Collins | | B05C 3/09 |
| | | | | 118/423 |
| 7,455,733 B2 * | 11/2008 | Lee | | B05D 7/22 |
| | | | | 118/66 |
| 8,616,152 B2 * | 12/2013 | Chen | | B05B 12/122 |
| | | | | 118/313 |
| 8,746,168 B2 * | 6/2014 | Abbasian | | C09D 4/00 |
| | | | | 118/423 |
| 8,967,077 B2 * | 3/2015 | Abbasian | | A61L 29/085 |
| | | | | 118/423 |
| 9,096,923 B2 * | 8/2015 | Clinton | | C23C 18/125 |
| 9,221,071 B2 * | 12/2015 | Huang | | C23C 18/00 |
| 9,346,632 B2 * | 5/2016 | Noda | | B65G 49/0477 |
| 9,811,096 B2 * | 11/2017 | Hayashi | | G05D 9/12 |
| 9,834,834 B2 * | 12/2017 | Yamauchi | | C23C 2/06 |
| 9,950,332 B2 * | 4/2018 | McQueen | | B05B 7/1486 |
| 9,957,585 B2 * | 5/2018 | Takahashi | | C22C 38/002 |
| 9,962,726 B2 * | 5/2018 | Park | | B05C 3/132 |
| 9,987,654 B2 * | 6/2018 | Murata | | D06B 3/12 |
| 10,487,414 B2 * | 11/2019 | Noda | | C25D 17/02 |
| 10,513,779 B2 * | 12/2019 | Utsumi | | B05C 5/007 |
| 10,543,501 B2 * | 1/2020 | McQueen | | B05B 7/1486 |
| 10,576,492 B2 * | 3/2020 | Utsumi | | C23C 18/168 |
| 10,640,875 B2 * | 5/2020 | Kohtoku | | H05K 999/99 |
| 10,844,484 B2 * | 11/2020 | Jdira | | C23C 16/4481 |
| 10,995,407 B2 * | 5/2021 | Utsumi | | C23C 18/1628 |
| 11,001,928 B2 * | 5/2021 | Utsumi | | C23C 18/1628 |
| 11,001,929 B2 * | 5/2021 | Utsumi | | B05C 5/007 |
| 11,203,036 B1 * | 12/2021 | Lin | | B05C 13/02 |
| 11,213,849 B2 * | 1/2022 | Choi | | B05C 9/14 |
| 11,285,507 B2 * | 3/2022 | Choi | | B05C 13/02 |
| 2013/0122704 A1 * | 5/2013 | Kanda | | C23C 18/1675 |
| | | | | 118/712 |
| 2015/0013905 A1 * | 1/2015 | Nakagawa | | C23C 18/1619 |
| | | | | 156/345.23 |
| 2018/0117618 A1 * | 5/2018 | Utsumi | | B08B 11/02 |
| 2021/0206657 A1 * | 7/2021 | Vielma | | C02F 1/281 |
| 2021/0370340 A1 * | 12/2021 | Lin | | B05C 13/02 |

* cited by examiner

METHOD AND APPARATUS FOR COATING A DRINKING STRAW

BACKGROUND

Field of the Invention

The present invention relates to applying coatings to drinking straws, and more specifically, to an apparatus and associated method for applying coatings to all surfaces of pre-formed paper drinking straws.

Description of Related Art

A drinking straw is a utensil that is intended to carry the contents of a beverage to one's mouth. A straw is used by placing one end in one's mouth and the other in a beverage. By employing suction, the air pressure in one's mouth drops causing atmospheric pressure to force the liquid through the straw and into the mouth.

Straws are commonly made from plastics, but environmental concerns and new regulations have led to a rise in the popularity of biodegradable straws. Biodegradable straws are often made of paper, paperboard, or cardboard.

Paper straws are typically manufactured by cutting a large sheet of paper into strips and rolling the strips of paper in a spiral pattern to form a tube. One edge of each strip overlaps and is adhered to an opposite edge of the strip such that the resulting tube maintains its shape. Finally, excess material located at each end of the straw is cut to form the final straw. A disadvantage of paper straws is that paper absorbs water. As a paper straw absorbs water, either from a person or from a beverage, the paper straw becomes softer and less able to hold its shape.

To prevent water absorption, paper straws are typically made from paper that has been pre-coated with a water-resistant coating. Beginning with a sheet of paper that includes a pre-applied water-resistant coating on its surface, conventional manufacturing of water-resistant paper straws includes cutting the coated sheet of paper into strips, rolling the strips into tubes, and cutting the ends to form coated paper straws.

One problem with paper straws manufactured in this way, however, is that the water-resistant coating does not protect all surfaces of the straw from absorbing water. Because the water-resistant coating is applied to the sheet of paper before it is cut and formed into each individual straw, edges where the paper is cut are exposed and uncoated. The exposed edges of the straw include the ends of the straw as well as the overlapping spiral edge of the paper strip forming the straw. As a result, portions of conventional coated paper straws lack a water-resistant coating and expose the paper fibers to unwanted water absorption.

Accordingly, a need exists for improved methods and systems for manufacturing coated paper drinking straws.

SUMMARY

According to one embodiment of the present invention, an apparatus for coating a paper drinking straw is disclosed. The apparatus includes a dipping tank containing a liquid bath for coating an uncoated drinking straw when submerged in the bath and a straw engagement means for submerging the uncoated drinking straw in the bath. The straw engagement means may be a conveyor having one or more channels for holding and transporting the uncoated paper drinking straws through the bath. The apparatus may further include a dryer or other means for removing excess coating from the surface of the straws after being submerged in the bath.

According to another embodiment, a method for coating a drinking straw is disclosed. The method includes receiving an uncoated paper drinking straw and submerging the uncoated paper drinking straw in a bath containing a water-resistant coating. Excess coating is removed from the surface of the coated drinking straw after being submerged in the bath, for example, by an air or infrared dryer.

According to yet another embodiment, a drinking straw assembly is disclosed. The drinking straw assembly includes an elongate tubular body composed of a water-soluble material and a water-resistant coating. The water-resistant coating has been applied to all surfaces of the water-soluble material by submerging the elongate tubular body in a bath containing the water-resistant coating.

DETAILED DESCRIPTION

The subject matter described herein includes a method and an apparatus for coating a drinking straw, such as a pre-formed, uncoated paper drinking straw. The method includes submerging the uncoated drinking straw in a bath containing a water-resistant coating. Excess coating is then removed from the surface of the coated drinking straw after being submerged in the bath. For example, the uncoated straws may sit in a hopper of the apparatus. A wheel may turn a belt that has slots in it that each hold a straw. The belt may rotate and pick up a straw from the hopper. The belt then continues beneath the surface of the bath in a tub or dipping tank. In order to counteract a paper straw's natural tendency to float upwards while submerged in the bath (i.e., buoyancy) a wheel may be positioned partially submerged in the bath so that straws entering one side of the bath and exiting another side of the bath must be submerged when underneath the submerged portion of the wheel. When the straw emerges on the other side of the bath, it is dried and packaged for sale.

In contrast to conventionally coated drinking straws that use pre-coated paper sheets cut into strips used to form a straw thereby exposing edges of the paper where the paper is cut is, and exposing the paper to unwanted water absorption, the present invention applies a coating (e.g., a water-resistant coating) to a pre-formed, uncoated drinking straw. This results in complete coverage of all surfaces of the straw with the coating. The preset invention is also cheaper to manufacture than conventionally coated drinking straws because uncoated paper is lighter, cheaper, and more flexible than coated paper, which reduces transportation costs of the paper and is easier to shape into an elongated tubular form.

Figure 1:
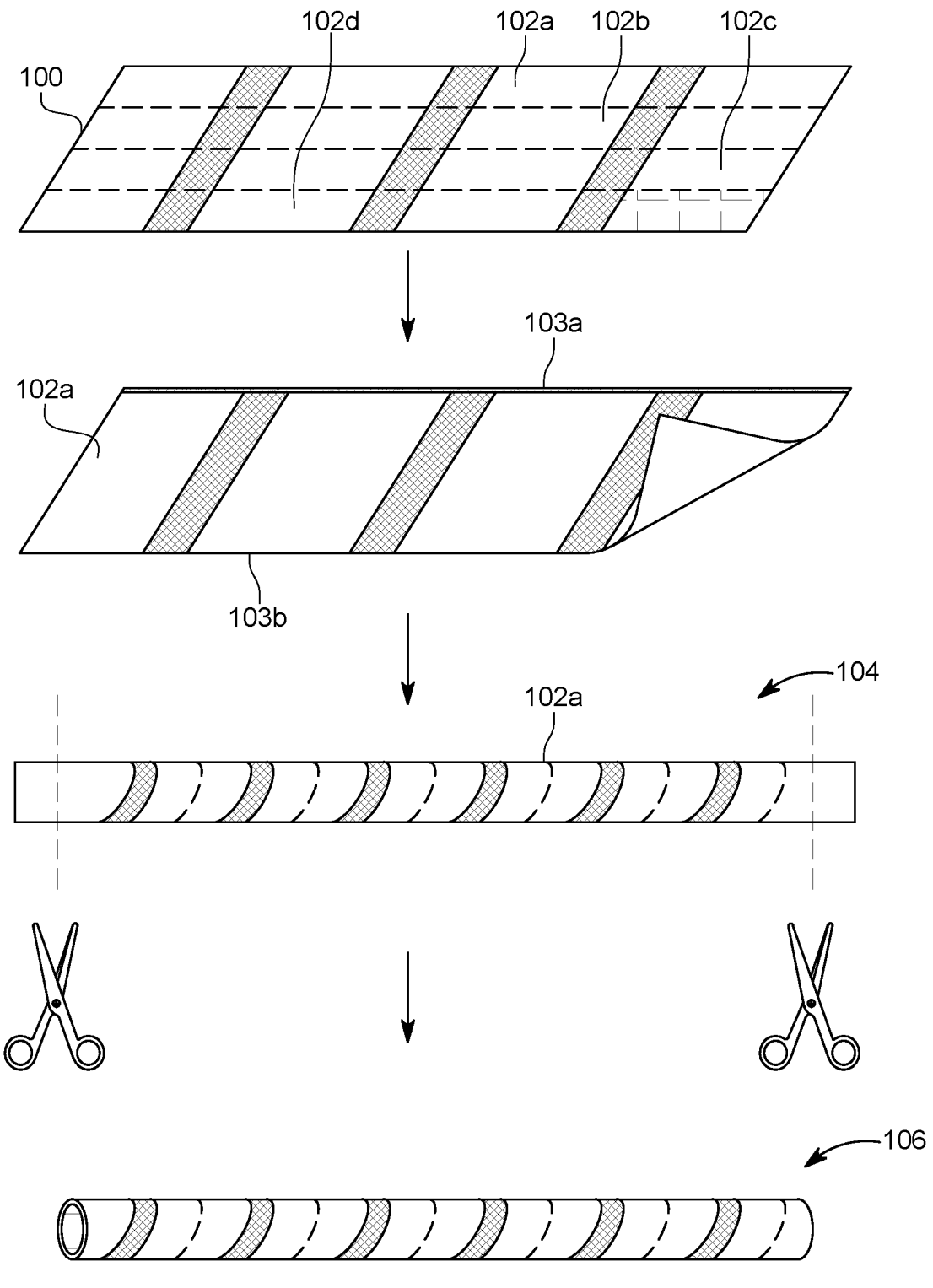
FIG. 1 is a diagram showing steps for producing a conventional paper straw according to the prior art.

FIG. 1 is a diagram showing steps for producing a conventional coated paper straw according to the prior art. Referring to FIG. 1, the process begins by cutting a sheet of coated paper 100 into strips 102a-d. Coated paper 100 may be pre-applied with a water-resistant coating for preventing water absorption into the fibers of the paper sheet. Each strip 102a-d may be used to form one or more straws.

Next, strip 102a is curled, beginning at a corner of the strip 102a, to form a tube or cylinder. Glue or other adhesive means is applied to edge 103a so that, as the tube is formed, the edge 103b of the strip 102a is secured. Once the entire length of strip 102a is curled and secured together to form a tube, the result is a raw straw 104. Raw straw 104 includes excess paper and/or an uneven shape as a result of curling the strip 102a on the bias in a spiral pattern. In order to remove this undesirable portion of raw straw 104 and produce a finished coated straw 106, each end of raw straw 104 is cut perpendicular to the long axis of the straw. As will be discussed below with respect to FIG. 2, however, the conventional finished coated straw 106 includes exposed edges where strip 102a was cut from coated sheet of paper 100.

Figure 2:
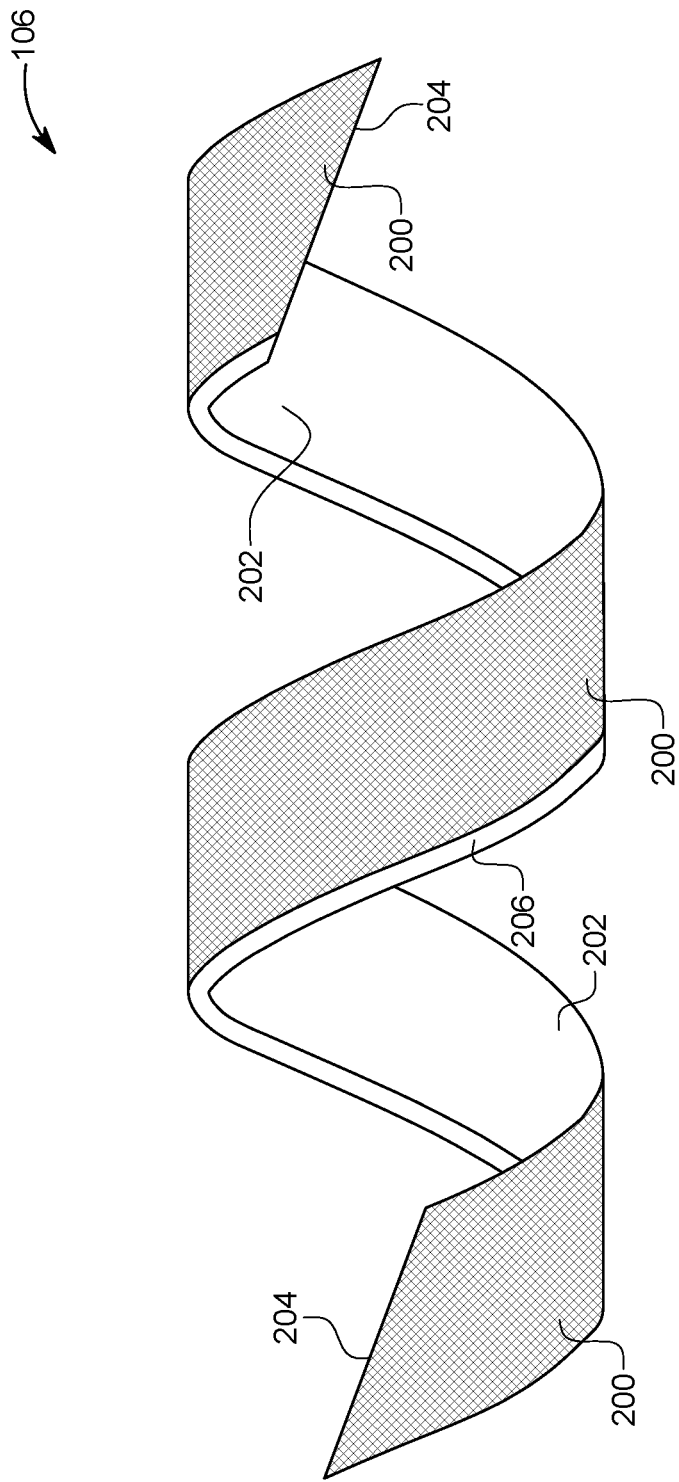
FIG. 2 is an exploded perspective view of a conventional paper straw according to the prior art.

FIG. 2 is an exploded perspective view of a conventional coated paper straw according to the prior art. Referring to FIG. 2, conventional coated paper straw is shown partially unwound or disassembled in order to better illustrate the exposed, or uncoated, portions of the straw. Because the outside surface of straw 106 corresponds to a coated surface of paper sheet 100, these portions 200 are coated. The same is true of the interior portion 202 of the straw 106, as it corresponds to the opposite, also coated, side of sheet of paper 100.

However, end portions 204, that were cut after the straw 106 was formed, are not coated because the coating was applied to sheet 100 before cutting the raw straw 104 into the finished straw 106. This exposes the interior paper fibers of end portions 204 to undesirable water absorption. Similarly, the overlapping paper edge 206, which corresponds with one of edges 103a or 103b of strip 102a, is also not coated because the coating was applied to sheet 100 before cutting the sheet of paper 100 into the strips 102a-d. This also exposes the interior paper fibers of edges 206 to undesirable water absorption. It may be appreciated that uncoated edges 106 may be exposed in either the interior or the exterior of the straw 106, depending on the direction of the spiral.

Figure 3:
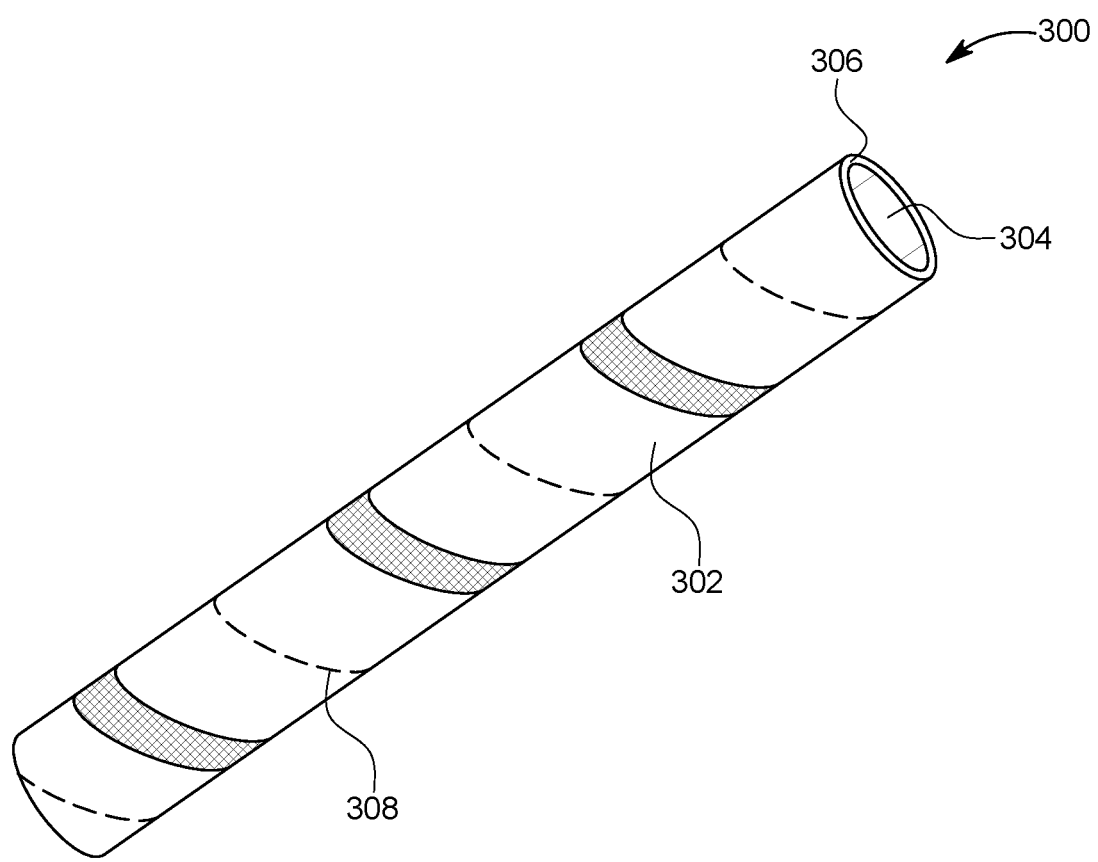
FIG. 3 is a perspective view of a coated paper straw according to an embodiment of the subject matter described herein.

FIG. 3 is a perspective view of a coated paper straw according to an embodiment of the subject matter described herein. Referring to FIG. 3, a straw 300 may be produced in a similar manner as conventional coated straw 106, however, in contrast to straw 106, straw 300 may be produced from an uncoated sheet of paper. An uncoated straw is cheaper to produce than a conventional coated straw 106 because uncoated sheets of paper are cheaper than coated sheets of paper. Moreover, pre-coated sheets of paper are typically heavier, thicker, and less pliable than uncoated sheets of paper, and may incur additional costs and complications when manufacturing straws.

In contrast to conventionally coated paper straws, straw 300 begins with uncoated paper. The straw 300 is then coated, for example by dipping the straw in a liquid bath, such that the coating covers all surfaces of the straw 300. For example, an outer surface 302 and an interior surface 304 of the straw 300 are coated. While both a conventional coated straw and straw 300 include coatings on their inner and outer surfaces 300 and 302, in contrast to conventional coated straws which do not include coating on the ends or seams of the straw, the ends 306 and seams 308 of straw 300 are coated. This is because the coating is applied after the straw 300 is created rather than before (i.e., uncoated paper is formed into straws and then dipped in coating rather than coated paper that is cut and then formed into straws). By coating a pre-made straw 300 rather than creating a straw from pre-coated paper sheets, the present invention allows all surfaces of the straw 300 to be coated. In embodiments where the coating is a water-resistant coating, this allows all surfaces of the straw 300 to be protected from water penetration.

Instead of, or in addition to, a water-resistant coating as described herein, straws according to the present disclosure may also be coated with a water-soluble coating. For example, a drinking straw may be made of an insoluble material, such as metal or plastic, and may be coated with a water-soluble coating. Alternatively, a drinking straw may be made of a water-soluble material, such as paper, and first coated with a water-resistant coating and subsequently coated with one or more water-soluble coatings. It is appreciated that any number of coatings may be applied to a drinking straw without departing from the scope of the subject matter described herein. For example, the straw may be submerged in a first bath containing a first coating, the first coating may be dried, and then the straw may be submerged in a second bath containing a second coating, etc.

Various additives may also be included as part of the water-soluble coating such that the additive(s) may be released from suspension in the coating when the coating is dissolved by exposure to water. For example, a drinking straw may include an additive coating which progressively dissolves, breaks down or erodes in a fluid being drawn through the straw in use. The additive coating may include sweeteners, flavorings, colorants, vitamins, stimulants, dietary supplements (e.g., collagen, fat busters, and the like), probiotics and/or pharmaceutical products (e.g., pain relievers, analgesics, and the like). In order to prevent the additive coating from dissolving too quickly or too slowly, thereby either imparting a weak flavor and/or color to a beverage or providing too strong a dose of vitamins and/or pharmaceuticals, the solubility of the additive coating may be customized for different applications. In one embodiment, the thickness and/or the composition of the additive coating may be configured to fully dissolve within five minutes when submerged in a cold beverage. In another embodiment, the thickness and/or the composition of the additive coating may be configured to fully dissolve within one minute when submerged in a hot beverage.

Many pharmaceutical compounds can be held within the additive coating and released into the liquid as the additive coating breaks down or dissolves on passage of the liquid through the straw. The compounds may dissolve into the liquid, or may be suspended, but will be drawn into the user's mouth to be ingested. This can provide a more convenient form for some patients to take certain medications, as an alternative to swallowing tablets. The active agent may also include nutritional compounds, which again may be dissolved into the liquid or be suspended as the coating dissolves into liquid drawn through the straw. The proportions of the coating and the active agent may vary based on the active agent and the volume of liquid in which it is desired that the coating will dissolve. The coating can also be designed to dissolve in a predetermined volume of liquid. For example, additive coatings that include a pharmaceutical substance may be configured to dissolve in a relatively small volume of liquid (e.g., 0-150 ml), so that they can be quickly and easily consumed by the user.

The additive coating described above may be added directly to the water-resistant coating such that the additives are part of the water-resistant coating and are added to the straw in a single dipping pass or process, or they may be added as a second step such that the water-resistant coating is added first, and then the additive coating is applied as a second coating on top of the water-resistant coating in a second dipping pass or process. Adding the additive coating as a second coating may allow for the additives to dissolve off of the straw into the liquid at a different rate than the underlying water-resistant coating.

Figure 4:
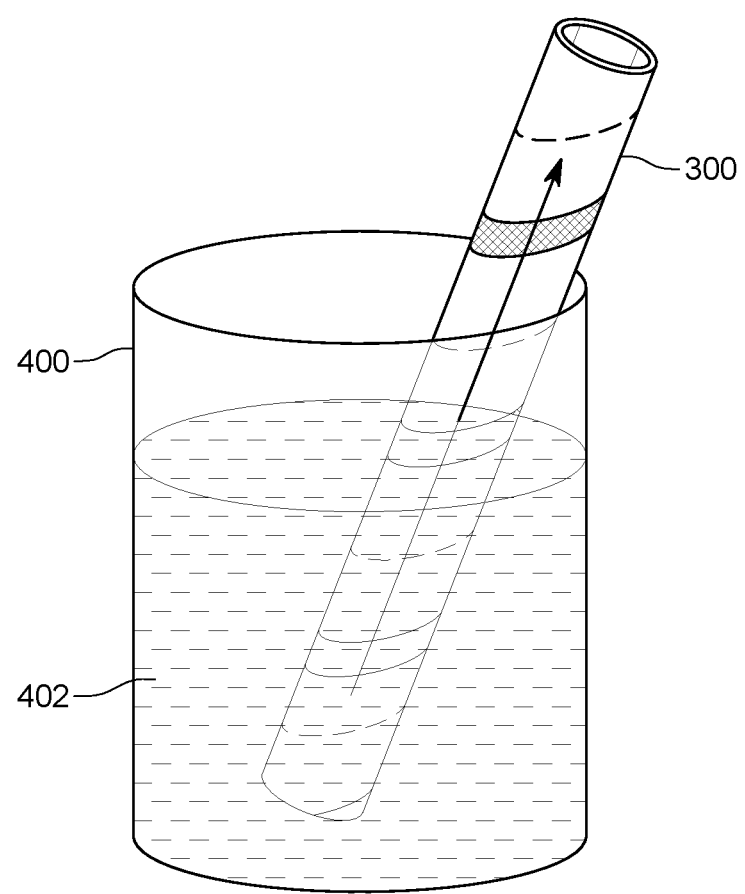
FIG. 4 is a perspective view of a drinking glass and a coated paper straw illustrating exemplary use of the coated paper straw according to an embodiment of the subject matter described herein.

FIG. 4 is a perspective view of a drinking glass and a coated paper straw illustrating exemplary use of the coated paper straw according to an embodiment of the subject matter described herein. Referring to FIG. 4, a drinking glass 400 may contain a liquid 402 for drinking through the coated straw 300. In one embodiment, the coating is a water-resistant coating that protects the fibers of the straw from absorbing the liquid 402. In this embodiment, the coating does not contain any additives such as colors, vitamins, or cannabinoids.

In another embodiment, the coating may contain additives such as sweeteners, flavorings, colorants, vitamins, cannabinoids, stimulants, dietary supplements (e.g., collagen, fat busters, and the like), probiotics and/or pharmaceutical products (e.g., pain relievers, analgesics, and the like). Depending on the additive, the coating may dissolve over time when exposed to liquid 402. For example, the coating applied to the straw 300 may contain a dose of THC or CBD. When the user drinks liquid 402 through the straw 300, a portion of the coating may dissolve and release an amount of THC or CBD contained therein. It is appreciated that the rate of dissolution may be affected by, for example, the temperature of the liquid 402 and/or the length of time the coating is exposed to the liquid 402.

When the interior surface of the straw 300 is exposed to the liquid 402 when drinking through the straw 300, as the liquid 402 travels through the straw 300, the coating and any additives may be dissolved into the liquid 402 and carried through the straw 300.

Additionally, the exterior surface of a bottom portion of the straw 300 submerged in the liquid 402 may also be exposed to the liquid 402. The outer coating of the straw 402, and any additives contained therein, may also be dissolved into the liquid 402 before being carried through the straw 300.

Finally, the exterior surface of an upper portion of the straw 300 may be exposed to water on the lips of the user drinking from the straw 300. This outer coating of the straw 402, and any additives contained therein, may be dissolved by the user's saliva, and received directly in the mouth rather than being first dissolved into the liquid 402.

Figure 5:
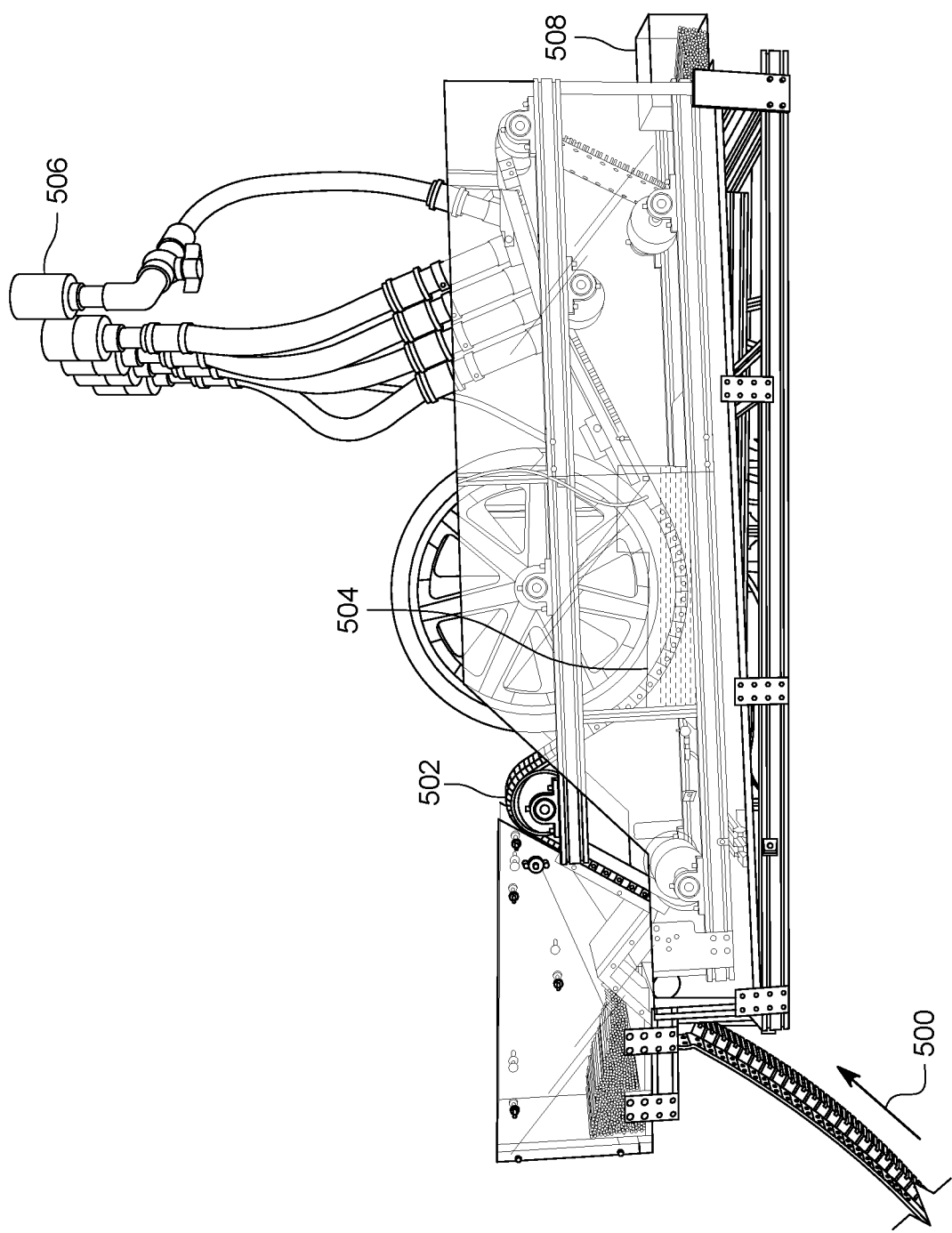
FIG. 5 is a side view illustrating a process for coating a premade paper straw according to an embodiment of the subject matter described herein.

FIG. 5 is a side view illustrating a process for coating a premade paper straw according to an embodiment of the subject matter described herein. Referring to FIG. 5, uncoated pre-made straws 500 may be transported by conveyor 502 into a dipping area 504. The dipping area 504 may contain a liquid solution for coating the uncoated straws 502. In order to ensure that the straws 500 are fully submerged for a desired period of time, a holding means or straw engagement means may be used to prevent the straw from floating to the top of the liquid solution in the dipping area 504. Once the straws have been coated, inside, outside, and at each end, excess coating may be dried from the straws. For example, a series of one or more air blowers may blow air downward into the straws as they exit the dipping area 504. Alternatively, infrared heat lamps may be used to dry or cure the coating on the straws. After drying, the finished coated straws 508 may be gathered and stored for packaging and shipping. In various embodiments, the finished coated straws 508 may be run through the process one or more additional times to add one or more additive coatings on top of the previously applied coating(s). A more detailed example of a machine for coating straws is described below with respect to FIG. 6.

Figure 6:
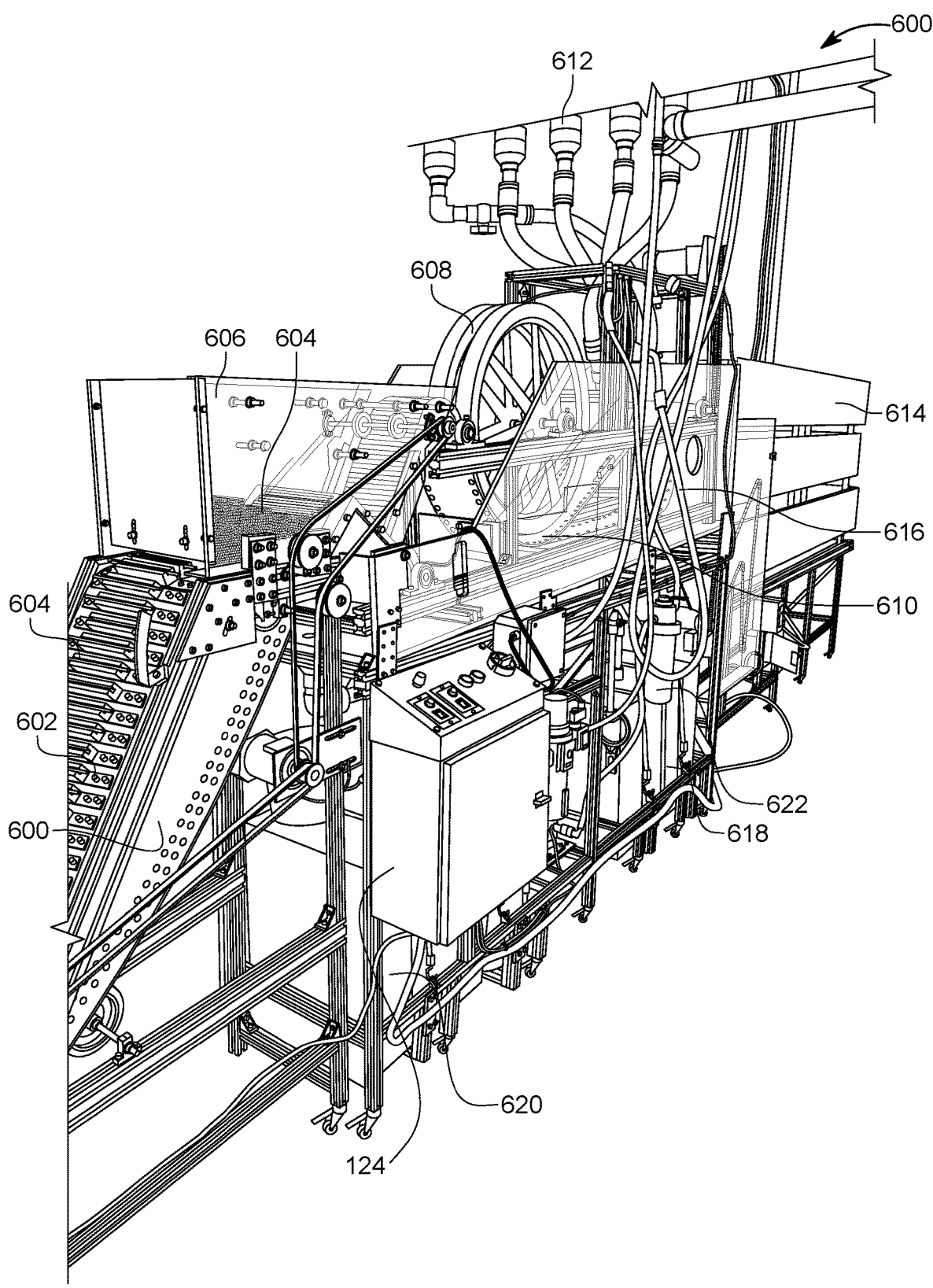
FIG. 6 is a perspective view of a machine for coating premade paper straws according to an embodiment of the subject matter described herein.

FIG. 6 is a perspective view of a machine for coating premade paper straws according to an embodiment of the subject matter described herein. Referring to FIG. 6, apparatus 600 for coating paper straws is shown. The process begins by receiving one or more uncoated paper straws 604 into grooves on conveyor belt 602. The conveyor belt 602 may be a rubberized material having horizontal channels sized such that one straw fits in each channel The conveyor belt 602 carries the straws upwards (left to right in FIG. 6) and deposits the straw 604 into a collection area 606. In one embodiment, the belt 602 may be 7.5 inches wide and approximately 14 feet 4 inches in length, with approximately 126 channels in the belt 602; however, a person having ordinary skill in the art will recognize that other dimensions may be used in accordance with the principles described herein.

From the collection area 606, uncoated straws 604 may again be transported by the conveyor belt 602 to a dipping tank 610. The dipping tank 610 may be surrounded on five sides (i.e., bottom, left, right, front, back) by plexiglass or other nonpermeable walls. The dipping tank 601 contains a liquid solution for coating the uncoated paper drinking straws when submerged in the liquid solution.

A straw engagement means 608 holds the uncoated paper drinking straws submerged in the dipping tank 610 for a preconfigured time. For example, a large rotating wheel 608 may be positioned such that a lower portion of the wheel 608 is submerged in the tank 610 but not touching the bottom of the tank 610. This allows the conveyor belt 600 and the straws 604 to pass under the wheel 608 as they are submerged in the solution. The straws exit the dipping tank 610 as the conveyor belt 602 rises above the level of the liquid solution. The wheel 608 may or may not engage and drive the belt 602. Additionally, the wheel 608 may include channels such that the liquid solution in the dipping tank 610 stays in the dipping tank 610 as the wheel 608 rotates and the liquid solution is not captured by the wheel 608. In one embodiment, the wheel 608 may have a diameter of approximately 26 inches; however, a person of ordinary skill will recognize that other dimensions may be used in accordance with the principles described herein. The wheel 608 may be driven, for example, by an electric motor, either directly or through one or more pulleys.

In one embodiment, the liquid bath in the dipping tank 610 contains a water-resistant coating. As mentioned above, the hydrophilicity of untreated paper-based materials limits their use as drinking straws and, as a result, biodegradable water-resistant paper for food-contact applications may be used. For example, the water-resistant coating may use melamine as a primer, which is FDA approved for food-contact applications. The coating of paper with water-repellent materials may then use compounds with low surface energies, such as fluorinated polymers, polysiloxanes (23,24) or higher alkanes, which are applied to create a hydrophobic coating for paper. Alternatively, polysiloxanes and higher alkanes may be used due to their nontoxic nature, affordability, and environmental friendliness. Finally, due to their lower surface tension, polysiloxanes may be used for greater hydrophobicity than is offered by higher alkanes. For example, a water-repellent outer layer may be applied to a paper straw using poly(dimethylsiloxane) (PDMS)—isocyanate. After the coating is applied, water absorption may be decreased as compared with uncoated paper.

In one embodiment, the bath contains a water-soluble supplement. For example, rather than solely providing water-resistance, a straw coated with a water-soluble supplement may allow for the supplement to be dissolved into a beverage consumed when using the straw. This allows for different formulations of the liquid solution in the bath to produce straws customized for particular applications. As will be discussed in greater detail below, applications include coloring a beverage being consumed and/or receiving a dose of a vitamin or cannabinoid as the supplement is released from the coating as the coating dissolves when exposed to water.

In one embodiment, the water-soluble supplement contains a cannabinoid such as cannabidiol (CBD) or tetrahydrocannabinol (THC). In another embodiment, the water-soluble supplement contains one or more vitamins In yet another embodiment, the water-soluble supplement contains dye for coloring a liquid that the straw is submerged into. In yet another embodiment, the water-soluble supplement contains a dietary supplement or a pharmaceutical supplement, as described above.

Once the straws 604 have been submerged and coated in the tank 610, the straws may be dried. Dryer 612, which may include one or more air blowers, may remove excess coating from the surface of the straws after being submerged in the liquid solution. In one embodiment, the dryer 612 blows air downward such that excess coating is captured by a waste catcher 616. The waste catcher 616 catches excess coating and may be coupled to a waste tank 618 for collecting the excess coating (i.e., caught waste) removed from the straws. Filter 622 may filter the caught waste from the waste tank 618. The filtered waste may be pumped from the waste tank 618 to a clean tank 620 for storage. Clean tank 620 may hold the filtered waste. The clean tank 620 may be configured to feed or supply the dipping tank 610 with additional coating when the amount of coating in the dipping tank 610 falls below a threshold.

A control panel 624 may allow a user to control the operations of the apparatus 600. For example, control panel 624 may include a power on/off switch for starting or stopping the conveyor 600. Control panel 624 may also include a speed control for adjusting the speed of the conveyor 600. Control panel 624 may also include a power on/off switch for the pump and filter 622 in case the user wishes to control the operation of the pump/filter 622 independently from the conveyor 600.

Figure 7:
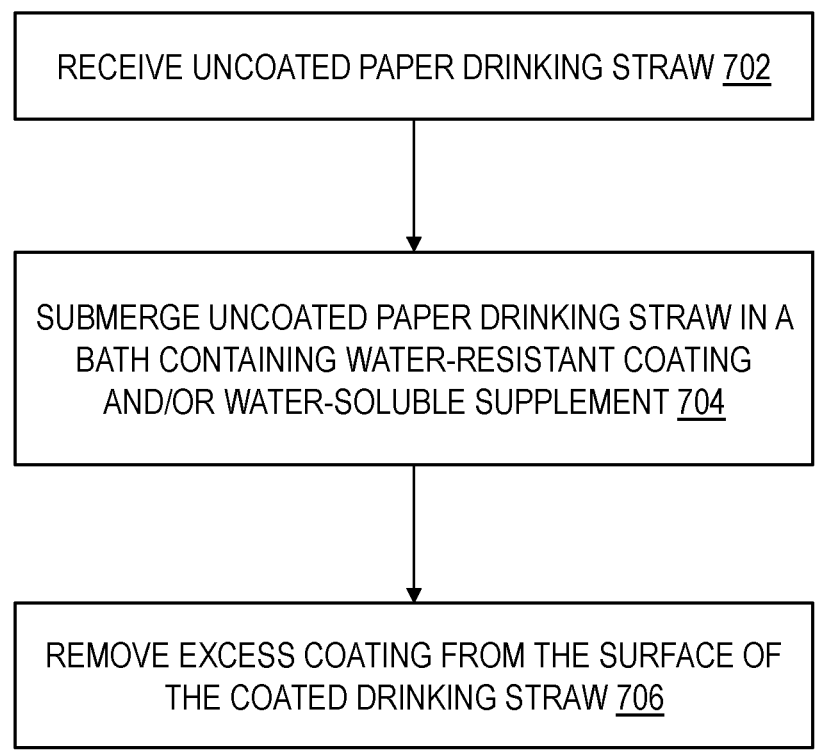
FIG. 7 is an example process flow coating premade paper straws according to an embodiment of the subject matter described herein.

FIG. 7 is an example process flow coating premade paper straws according to an embodiment of the subject matter described herein. Referring to FIG. 7, the method includes receiving an uncoated paper drinking straw, as step 702. The method further includes submerging the uncoated paper drinking straw in a bath containing a water-resistant coating, at step 704. In one embodiment, the bath may contain a water-soluble supplement, as described in detail above. The method further includes removing excess coating from the surface of the coated drinking straw after it has been submerged in the bath, at step 706.

The Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus for coating a drinking straw, the apparatus comprising:
    a dipping tank containing a liquid bath for coating all surfaces of the drinking straw when submerged in the liquid bath;

a conveyor belt configured to transport a plurality of drinking straws into the dipping tank for submersion in the liquid bath and out of the dipping tank after submersion in the liquid bath,
wherein the conveyor belt includes a plurality of grooves, with each groove configured to receive at least one drinking straw of the plurality of drinking straws,
wherein a portion of the conveyor belt is outside the dipping tank and a portion of the conveyor belt is in the dipping tank; and
a straw engagement means at least partially submerged in the dipping tank for submerging the plurality of drinking straws in the liquid bath and preventing the plurality of submerged drinking straws from floating out of the grooves of the conveyor belt; and
a blower positioned to blow excess coating from the surfaces of the plurality of drinking straws into a waste catcher to capture the excess coating after the plurality of drinking straws have been submerged in the liquid bath.

2. The apparatus of claim 1, wherein each drinking straw of the plurality of drinking straws comprises an elongate tubular body composed of a water-soluble material.

3. The apparatus of claim 2, wherein the water-soluble material includes one of paper, paperboard, or cardboard.

4. The apparatus of claim 1, further comprising a waste tank coupled to the waste catcher for collecting the excess coating from the surfaces of the plurality of drinking straws as caught waste after the plurality of drinking straws have been submerged in the liquid bath.

5. The apparatus of claim 4, further comprising a filter for filtering the caught waste in the waste tank.

6. The apparatus of claim 5, further comprising a clean tank for storing the filtered waste.

7. The apparatus of claim 6, wherein the clean tank supplies the dipping tank with the filtered waste as additional coating when the liquid bath in the dipping tank falls below a threshold.

8. The apparatus of claim 1, wherein the liquid bath contains a water-soluble supplement.

9. The apparatus of claim 8, wherein the water-soluble supplement contains one of cannabidiol (CBD) or tetrahydrocannabinol (THC).

10. The apparatus of claim 8, wherein the water-soluble supplement contains one or more vitamins.

11. The apparatus of claim 8, wherein the water-soluble supplement contains dye for coloring the liquid bath.

12. The apparatus of claim 1, further comprising an infrared dryer positioned to dry or cure the coating on the plurality of drinking straws after the plurality of drinking straws have been submerged in the liquid bath.

13. The apparatus of claim 12, wherein the conveyor belt transports the plurality of drinking straws under the infrared dryer after submersion in the liquid bath.

14. The apparatus of claim 1, further comprising a deposit area into which the plurality of drinking straws are deposited after being coated in the liquid bath.

15. The apparatus of claim 14, wherein the conveyor belt transports the plurality of drinking straws out of the liquid bath to the deposit area and allows the plurality of drinking straws to fall from the conveyor belt into the deposit area.

16. The apparatus of claim 1, further comprising a collection area outside the dipping tank, wherein the conveyor belt is further configured to receive the plurality of drinking straws at the collection area and transport the plurality of drinking straws from the collection area to the dipping tank.

17. The apparatus of claim 16, wherein the apparatus is configured such that the plurality of drinking straws fall into the grooves of the conveyor belt from the collection area as the conveyor belt passes the collection area.

18. The apparatus of claim 1, wherein the straw engagement means comprises a wheel positioned above the dipping tank, wherein the wheel engages the conveyor belt to cause the conveyor belt to be submerged into the dipping tank.

19. The apparatus of claim 18, wherein the wheel is positioned to avoid contact with a bottom surface of the dipping tank.

20. The apparatus of claim 1, wherein the straw engagement means further includes a plurality of channels positioned to receive a portion of the liquid bath from the dipping tank, wherein the plurality of channels is configured to keep the portion of the liquid bath in the dipping tank when the straw engagement means moves.

21. The apparatus of claim 1, wherein at least a portion of the conveyor belt is positioned higher than the liquid bath before the conveyor belt enters the liquid bath such that the conveyor belt enters the liquid bath at a downward angle.

22. The apparatus of claim 21, wherein the straw engagement means engages the conveyor belt to cause the conveyor belt to enter the liquid bath at the downward angle.

23. An apparatus for coating a drinking straw, the apparatus comprising:
a dipping tank containing a liquid bath for coating all surfaces of a plurality of drinking straws when submerged in the liquid bath;
a drying element positioned to dry the plurality of drinking straws after the plurality of straws emerge from the liquid bath; and
a conveyor belt including a plurality of grooves with each groove configured to receive at least one drinking straw of the plurality of drinking straws,
wherein a portion of the conveyor belt is outside the dipping tank and a portion of the conveyor belt is in the dipping tank,
wherein the conveyor belt transports the plurality of drinking straws into the dipping tank to be submerged in the liquid bath,
wherein the conveyor belt transports the plurality of drinking straws out of the dipping tank to the drying element after the plurality of straws have been submerged in the liquid bath, and
a wheel at least partially submerged in the dipping tank, wherein the wheel is configured engage the conveyor belt to prevent the plurality of drinking straws from floating to a surface of the liquid bath when submerged.

24. The apparatus of claim 23, wherein the wheel includes a plurality of channels positioned to receive a portion of the liquid bath from the dipping tank, wherein the plurality of channels is configured to keep the portion of the liquid bath in the dipping tank when the wheel rotates.

25. The apparatus of claim 23, further comprising:
a waste catcher for capturing excess coating from the surfaces of a coated drinking straw after being submerged in the liquid bath as caught waste,
a waste tank coupled to the waste catcher for collecting the caught waste,
a filter for filtering the caught waste in the waste tank, and
a clean tank for storing the filtered waste, wherein the clean tank supplies the dipping tank with the filtered waste when an amount of the liquid bath in the dipping tank falls below a threshold.

26. The apparatus of claim 23, wherein the drying element comprises an air blower or an infrared heat lamp.

\* \* \* \* \*